United States Patent [19]

Mikkola et al.

[11] Patent Number: 4,657,762
[45] Date of Patent: Apr. 14, 1987

[54] ANAEROBIC BACTERIAL PREPARATIONS OF INTESTINAL ORIGIN AND THEIR USE

[75] Inventors: Antti R. Mikkola, Kerava; Heli-Riitta M. Hakkinen, Helsinki; Lasse O. Nuotio, Helsinki; Esko V. Nurmi, Helsinki; Carita E. Schneitz, Helsinki, all of Finland

[73] Assignee: Farmos-Yhtyma Oy, Turku, Finland

[21] Appl. No.: 705,255

[22] Filed: Feb. 25, 1985

[30] Foreign Application Priority Data

Mar. 1, 1984 [FI] Finland .................................. 840816

[51] Int. Cl.$^4$ ...................... A61K 35/74; A61K 35/12; C12N 1/20
[52] U.S. Cl. ........................................ 424/93; 426/61; 426/71
[58] Field of Search ......................................... 424/93

[56] References Cited

U.S. PATENT DOCUMENTS

| | | | |
|---|---|---|---|
| 3,953,609 | 4/1976 | Farr | 424/93 X |
| 4,251,509 | 2/1981 | Hanson et al. | 424/93 X |
| 4,335,107 | 6/1982 | Snoeyenbos et al. | 424/93 |

FOREIGN PATENT DOCUMENTS

1151066  8/1983  Canada.

*Primary Examiner*—Howard E. Schain
*Attorney, Agent, or Firm*—Armstrong, Nikaido, Marmelstein & Kubovcik

[57] ABSTRACT

This invention provides a composition useful in the treatment or prophylaxis of disturbances in the normal intestinal bacteria flora in poultry. The composition is intended to be administered as an aqueous mixture and it contains anaerobic bacteria of intestinal origin and an agent, preferably cysteine, which decreases the toxic effect of the oxygen dissolved in the water, and preferably also a substantially neutral buffer.

6 Claims, No Drawings

ANAEROBIC BACTERIAL PREPARATIONS OF INTESTINAL ORIGIN AND THEIR USE

This invention relates to bacterial preparations which may be administered to poultry as an aqueous mixture for the treatment or prophylaxis of disturbances of the intestinal bacterial flora of poultry, such as may be caused, for example, by infection.

Healthy warm-blooded animals have an intestinal bacteria equilibrium typical of each species. Individual differences within the same species are usually caused by diet and the age of the animal. The equilibrium is generally stable and provides an essential buffer effect against external disturbances. Disturbances in the equilibrium can occur if one of the bacterial strains normally present in the balance, or a completely external bacterial strain, prevails over the others. This can be induced by disease or by the effect of antibiotics used in the treatment of disease. It can also result from food poisoning or an intestinal infection. Newly born or very young individuals of most species are especially liable to catch intestinal infections because their intestinal bacterial flora has not achieved a stable equilibrium.

The most important intestinal infection worldwide is salmonellosis, which is usually spread via poultry breeder-houses, especially via modern broiler breeder-houses.

Industrial broiler production cuts off the natural, coprophagous transfer of the anaerobic bacterial flora from adult birds to newly hatched chicks. During their first two weeks of life these chicks are especially sensitive to *Salmonella* infection. In order to cut off this spreading route, efforts have been made to develop preparations containing anaerobic bacteria, which are mixed with the first drinking water of the newly hatched chicks to accelerate the establishment of a salmonella-resistant intestinal flora. Finnish Patent Publication No. 59925 equivalent to European patent publication No. 33584 discloses such bacterial preparations effective in the prophylaxis of *Salmonella* infections. Other bacterial preparations are disclosed in European Patent Publication No. 6695. The rapid establishment of a balance in the normal intestinal flora increases the growth rate of the chicks and improves the economy of the feed usage.

There are principally two kinds of preparation for the treatment or prophylaxis of disturbances in the normal bacteria flora. One kind typically contains nutrients, e.g. special sugars, which selectively enhance the growth of certain bacterial species belonging to the normal flora or supporting that flora. Such preparations are useful especially in the restoration and support of a previously existing equilibrium.

The other type of preparation comprises living anaerobic bacteria either in the form of a whole normal flora or a representative selection thereof. The use of such preparations essentially accelerates the establishment of a stable equilibrium of the normal flora in very young individuals and in individuals in which there have been serious disturbances in the flora. Some preparations of this kind contain only one bacterial species, and are therefore only suitable for the treatment of slight disturbances.

The majority of the normal intestinal microbes are obligate anaerobes. Unlike facultatively anaerobic or oxygen tolerant anaerobic bacteria, they are very sensitive to the toxic effect of oxygen. It is therefore most important to arrange their cultivation conditions so that this effect is minimized. The toxic effect of oxygen is related to the metabolism of the cells, and therefore, e.g., lyophilized cells, which have a very slow metabolism, are far less sensitive than actively growing cells to the toxic effect of oxygen. When the water content of the cells increases at a suitable temperature, the metabolism starts again and the sensitivity to oxygen returns.

In the use of such a preparation, which contains lyophilized cells and which is to be mixed with water, it is important to protect the cells against the effect of dissolved oxygen, especially if the preparation is mixed with water a long time before it is to be used.

The present invention provides a bacterial preparation for the treatment or prophylaxis of intestinal bacterial disturbances in poultry comprising at least one strain of anaerobic bacteria of intestinal origin and an agent which is non-toxic to the said bacteria and which reacts with any oxygen present without generating any product toxic to the said bacteria. The said agent reacts with any oxygen present and this prevents the oxygen from having a toxic effect on the cells. Suitable such agents are thiols and especially cysteine, usually in an amount from 0.05 to 0.3% based on the total solids content of the preparation. Because the effect of cysteine is dependent on the acidity of the solution, a buffer should also be provided to maintain the PA of the preparation at a nearly neutral pH-value and normally in the range 6–8. A phosphate buffer of essentially neutral pH is preferred.

The method of protecting obligately anaerobic bacteria according to the present invention is particularly suitable for use with preparations of the kinds mentioned in the aforesaid European Specifications, because there may be several hours from the moment when the preparation is mixed with water until the chick drinks the frist water.

The preparation may itself be supplied to the user in deep frozen or lyophilized (freeze-dried) form.

The invention includes within its scope a method for the treatment or prophylaxis of intestinal disturbances in poultry which comprises administering thereto an effective amount of a preparation of the invention.

The following Examples illustrate the invention.

EXAMPLE 1

The bacterial cell mass, which has been produced according to the method (example 1) described in the European publication 33584, separated from the cultivation medium and deep-frozen to $-70°$ C., is thawed. Using for the dilution either untreated tap water or tap water containing 0.05 mol $dm^{-3}$ of a phosphate buffer at pH 7.0 containing 0.25% (weight/volume) of L-cysteine (Merck, D-6100 Darmstadt BRD product no 2838), the cell mass is diluted to a cell density of $1.5 \times 10^8$/ml and successive ten-fold dilutions from this one. The one-day-old broiler chicks are divided into groups of six chicks per group, and 1 ml of each solution per group is administered directly into the crop of the chicks. One group is kept as control and receives no solution treatment. After one day the chicks are infected with *Salmonella infantis* by administering approximately 1000 cells directly into the crop. Thereafter the chicks are bred for 5 days getting feed containing no coccidiostatic compounds and fresh water ad. lib. On the sixth day the chicks are asphyxiated by carbon monoxide gas, and from the contents of their caeca the amount of salmonella organisms are determined by incubation of $10^{-4}$, $10^{-6}$ and $10^{-8}$ dilutions of the contents of the caeca on BTB-LS and SS Onoz media (See Schneitz C et al., Acta Path. Microbiol. Scand. Sect. B 89:109–116, 1981; and Onoz E & Hoffmann K, Zbl. Bakt. Hyg. I Abt. Orig. A 240: 16–21, 1978) which are cultivation media selective for salmonella. Salmonella organisms are also enriched from the contents of the caeca in a selenite broth (Leifson, E, Am. J. Hyg. 24:423–432, 1936) from which the cultivation is made, e.g., on BTB-LS and SS-onoz cultrivation media. The results of the experiment are shown in Table 1.

TABLE 1

The effect of cysteine on the efficiency of the anaerobic cell mass in inhibiting Salmonella colonization of the caeca of broiler chicks.
_Salmonella infantis_, unit/g caeca content

| Broiler chick | Dilution in tap water (weight ratio cell mass:water) | | Dilution in buffered cysteine-containing tap water (weight ratio cell mass:water) | | | Control |
|---|---|---|---|---|---|---|
| | 1:70 | 1:7000 | 1:70 | 1:700 | 1:7000 | |
| 1 | $R^a$ | $10^6$ | $—^b$ | — | $10^8$ | $10^8$ |
| 2 | $10^8$ | $10^4$ | — | R | $10^6$ | $10^8$ |
| 3 | $10^8$ | $10^6$ | — | — | $10^6$ | $10^8$ |
| 4 | $10^6$ | $10^8$ | — | — | $10^8$ | $10^8$ |
| 5 | $10^8$ | $10^6$ | — | — | $10^8$ | $10^8$ |
| 6 | $10^6$ | $10^6$ | — | — | $10^8$ | $10^8$ |

$^a$salmonella found in the enriched cultivation
$^b$salmonella not found in the diluted or enriched cultivation

EXAMPLE 2

The bacteria cell mass produced according to the method disclosed in European patent publication 33584 and separated from the cultivation medium is lyophilized. This lyophilized cell mass is either used as such or mixed with mono- and dipotassium hydrogenphosphates and L-cysteine (Merck, D-6100 Darmstadt BRD, product no 2838) in such amounts that dilution of the cell mass for the investigation of the salmonella-colonization prophylactive effect gives a solution containing 0.05 mol dm$^{-3}$ phosphate buffer at pH 7 and 0.25% (weight/volume) of L-cysteine. These cell masses are diluted with tap water to give mixtures containing 10 mg ml$^{-1}$ or 25 mg ml$^{-1}$ of cell mass. One-day-old broiler chicks are divided into groups of six chicks per group and 1 ml of each solution per group is intubated directly into the crop of the chicks. The control group is not treated with any solution. The test follows otherwise the experiment in Example 1. The test results obtained with one cell mass are shown in Table 2.

TABLE 2

The effect of cysteine on the efficiency of the lyophilized cell mass in inhibiting Salmonella colonization of the caeca of broiler chicks.
_Salmonella infantis_, unit/g caeca content

| Broiler chick | Cell mass containing no cysteine | | Cell mass mixed with cysteine | | Control |
|---|---|---|---|---|---|
| | 10 mg/ml | 25 mg/ml | 10 mg cell mass/ml | 25 mg cell mass/ml | |
| 1 | $R^a$ | $10^6$ | R | $—^b$ | $10^8$ |
| 2 | $10^4$ | R | $10^6$ | R | $10^8$ |
| 3 | R | $10^6$ | R | — | $10^8$ |
| 4 | $10^8$ | $10^6$ | — | — | $10^8$ |
| 5 | $10^8$ | R | — | — | $10^8$ |
| 6 | $10^6$ | no r.$^c$ | R | — | $10^8$ |

$^a$salmonella found in the enriched cultivation
$^b$salmonella not found in the diluted or enriched cultivation
$^c$no result

We claim:

1. A method for the treatment or prophylaxis of intestinal disturbances in poultry which comprises administering to said poultry in water an effective amount of a bacterial preparation comprising at least one strain of anaerobic bacteria of intestinal origin and an agent which is non-toxic to the said bacteria and which reacts with any oxygen present without generating any product toxic to the said bacteria, said agent being present in an amount effective to prolong the effectiveness of the said preparation.

2. A method according to claim 1, in which the said agent is a thiol.

3. A method according to claim 1, in which the said agent is cysteine.

4. A method according to claim 1, in which the proportion of the said agent is 0.05 to 0.3 percent based on the total solids content of the said preparation.

5. A method according to claim 1, which the preparation contains a non-toxic buffer to maintain the pH at 6 to 8.

6. A method according to claim 5 in which the said buffer is a phosphate buffer providing a pH of substantially 7.

* * * * *